United States Patent [19]

Hammersmark et al.

[11] Patent Number: 5,429,604
[45] Date of Patent: Jul. 4, 1995

[54] FIBER OPTIC CATHETER WITH TWISTABLE TIP

[75] Inventors: Dan J. Hammersmark, Colorado Springs, Colo.; Timothy J. Wood, San Luis Obispo, Calif.; Matthew S. Solar, Cooper City, Fla.

[73] Assignee: Spectranetics Corporation, Colorado Spring, Colo.

[21] Appl. No.: 335,955

[22] Filed: Nov. 3, 1994

Related U.S. Application Data

[63] Continuation of Ser. No. 31,391, Mar. 12, 1993, abandoned, which is a continuation-in-part of Ser. No. 853,607, Mar. 18, 1992, abandoned.

[51] Int. Cl.⁶ .................. A61M 37/00; A61B 1/00
[52] U.S. Cl. ........................ 604/95; 600/182
[58] Field of Search ............. 604/95, 96; 128/4, 6, 128/7, 657, 772

[56] References Cited

U.S. PATENT DOCUMENTS

| | | |
|---|---|---|
| Re. 33,166 | 2/1990 | Samson . |
| 4,197,666 | 4/1990 | Solar et al. . |
| 4,323,071 | 4/1982 | Simpson et al. . |
| 4,573,470 | 3/1986 | Samson et al. . |
| 4,582,181 | 4/1986 | Samson . |
| 4,619,263 | 10/1986 | Frisbie et al. . |
| 4,641,654 | 2/1987 | Samson et al. . |
| 4,664,112 | 5/1987 | Kensey et al. . |
| 4,664,113 | 5/1987 | Frisbie et al. . |
| 4,757,827 | 7/1988 | Buchbinder et al. . |
| 4,775,371 | 10/1988 | Mueller . |
| 4,795,458 | 1/1989 | Regan . |
| 4,798,586 | 1/1989 | Stevens . |
| 4,808,164 | 2/1989 | Hess . |
| 4,838,268 | 6/1989 | Keith et al. . |
| 4,841,976 | 6/1989 | Packard et al. . |
| 4,844,062 | 7/1989 | Wells . |
| 4,846,174 | 7/1989 | Willard et al. . |
| 4,867,173 | 9/1989 | Leoni . |
| 4,874,371 | 10/1989 | Comben et al. . |
| 4,898,577 | 2/1990 | Badger et al. . |
| 4,917,102 | 4/1990 | Miller et al. . |
| 4,923,462 | 5/1990 | Stevens . |
| 4,998,917 | 3/1991 | Gaiser et al. . |
| 4,998,923 | 3/1991 | Samson et al. . |
| 5,002,553 | 3/1991 | Shiber . |
| 5,007,896 | 4/1991 | Shiber . |
| 5,009,659 | 4/1991 | Hamlin et al. . |
| 5,024,651 | 6/1991 | Shiber . |
| 5,026,384 | 6/1991 | Farr et al. . |
| 5,030,204 | 7/1991 | Badger et al. . |
| 5,055,109 | 10/1991 | Gould et al. . |
| 5,059,176 | 10/1991 | Winters . |
| 5,083,549 | 1/1992 | Cho et al. ............... 128/7 |
| 5,114,403 | 5/1992 | Clarke et al. . |
| 5,167,220 | 12/1992 | Brown .................... 128/4 |
| 5,184,602 | 2/1993 | Anapliotis et al. ........ 128/6 |
| 5,185,004 | 2/1993 | Lashinski ............... 604/95 |
| 5,195,968 | 3/1993 | Lundquist et al. ....... 604/95 |
| 5,263,952 | 11/1993 | Grace et al. ............ 606/15 |

FOREIGN PATENT DOCUMENTS

| | | |
|---|---|---|
| 0377269 | 7/1990 | European Pat. Off. . |
| WO9109642 | 7/1991 | WIPO . |

*Primary Examiner*—John D. Yasko
*Assistant Examiner*—Adam J. Cermak
*Attorney, Agent, or Firm*—Cushman, Darby & Cushman

[57] ABSTRACT

The present invention is a catheter with a twistable tip. The catheter having a flexible wall for use in complex twisting anatomy contains a torque wire or a torquable guide wire lumen. The torque wire or torquable guide wire lumen extends through the length of the catheter and is attached to the catheter at or near the distal end thereof. The distal face of the catheter is angled to self align the catheter with an obstruction upon insertion. The proximal end of the torque wire protrudes from the proximal end of the catheter and is attached to a turn limiter. Rotation of the turn limiter imparts a torque to the torque wire or torquable guide wire lumen which is transmitted through the catheter to the distal end of the catheter where the applied torque twists the distal tip to manually align the tip with an obstruction. The twisting response at the tip of the catheter is determined by the torque applied to the torque element, the material and dimensional profile of the torque element, the attachment point of the torque element to the catheter and the material and dimensional profile of the catheter.

51 Claims, 7 Drawing Sheets

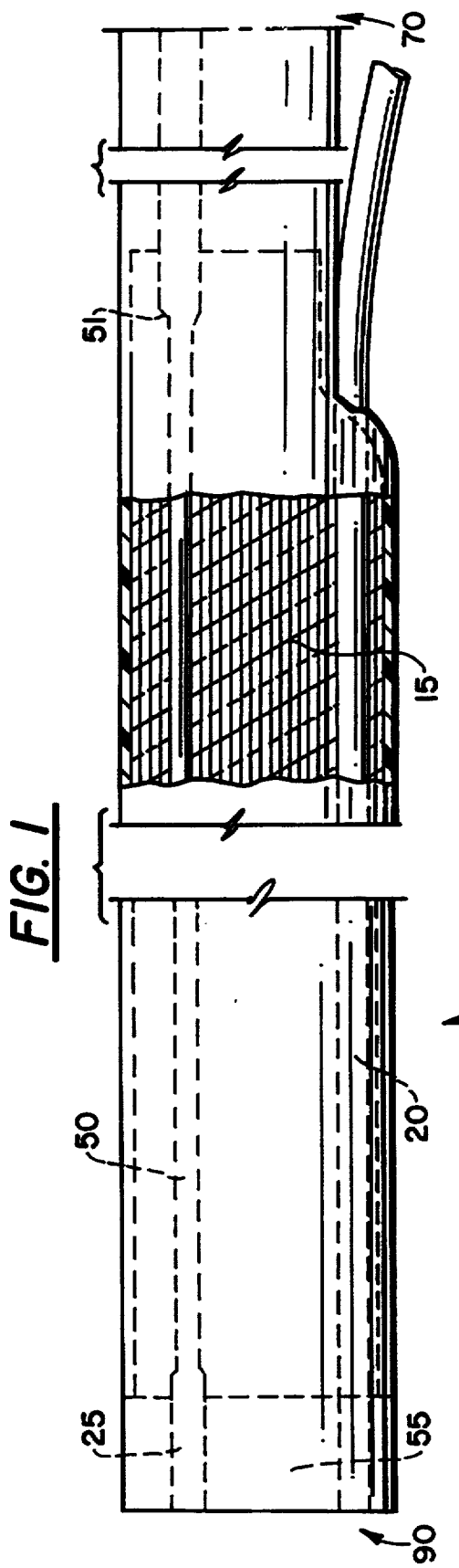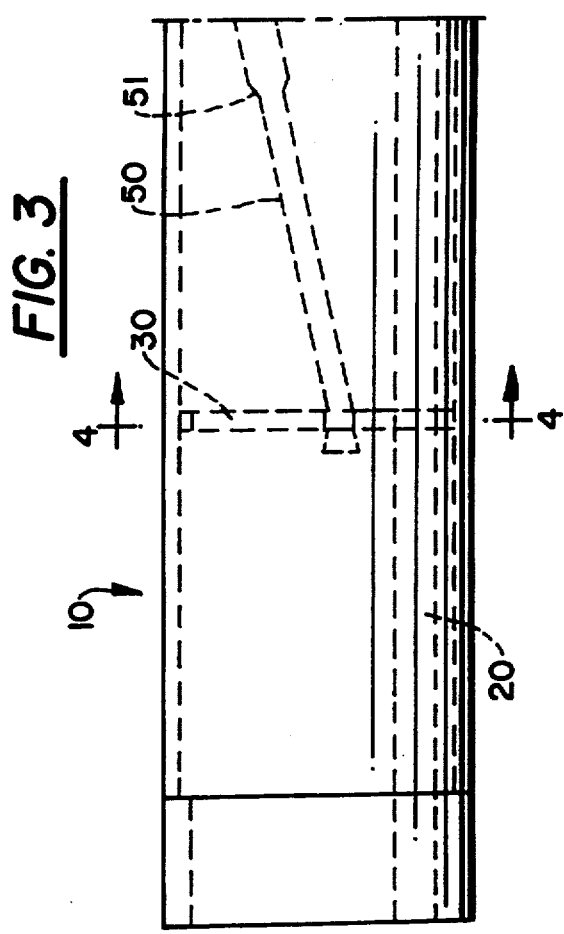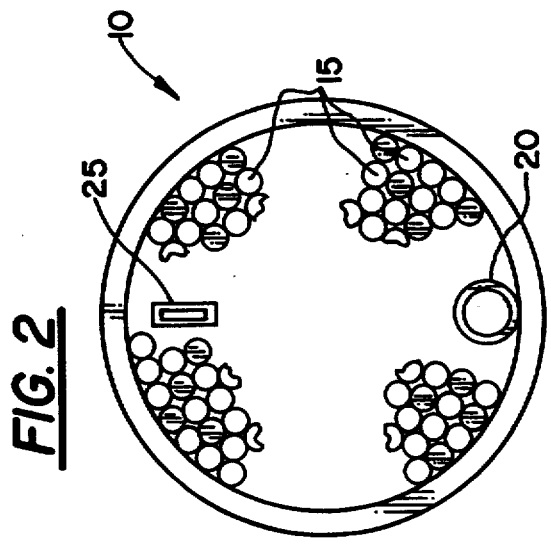

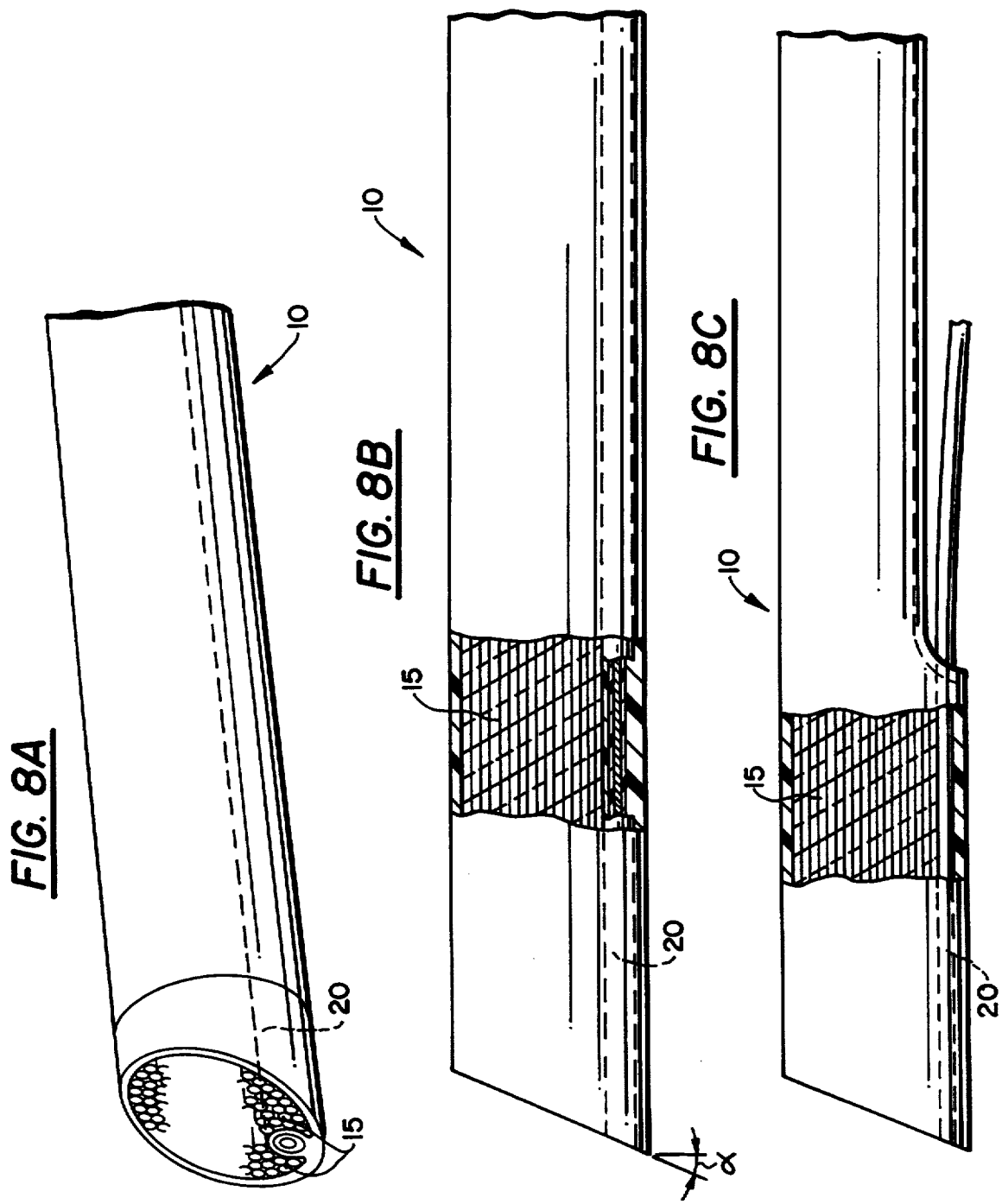

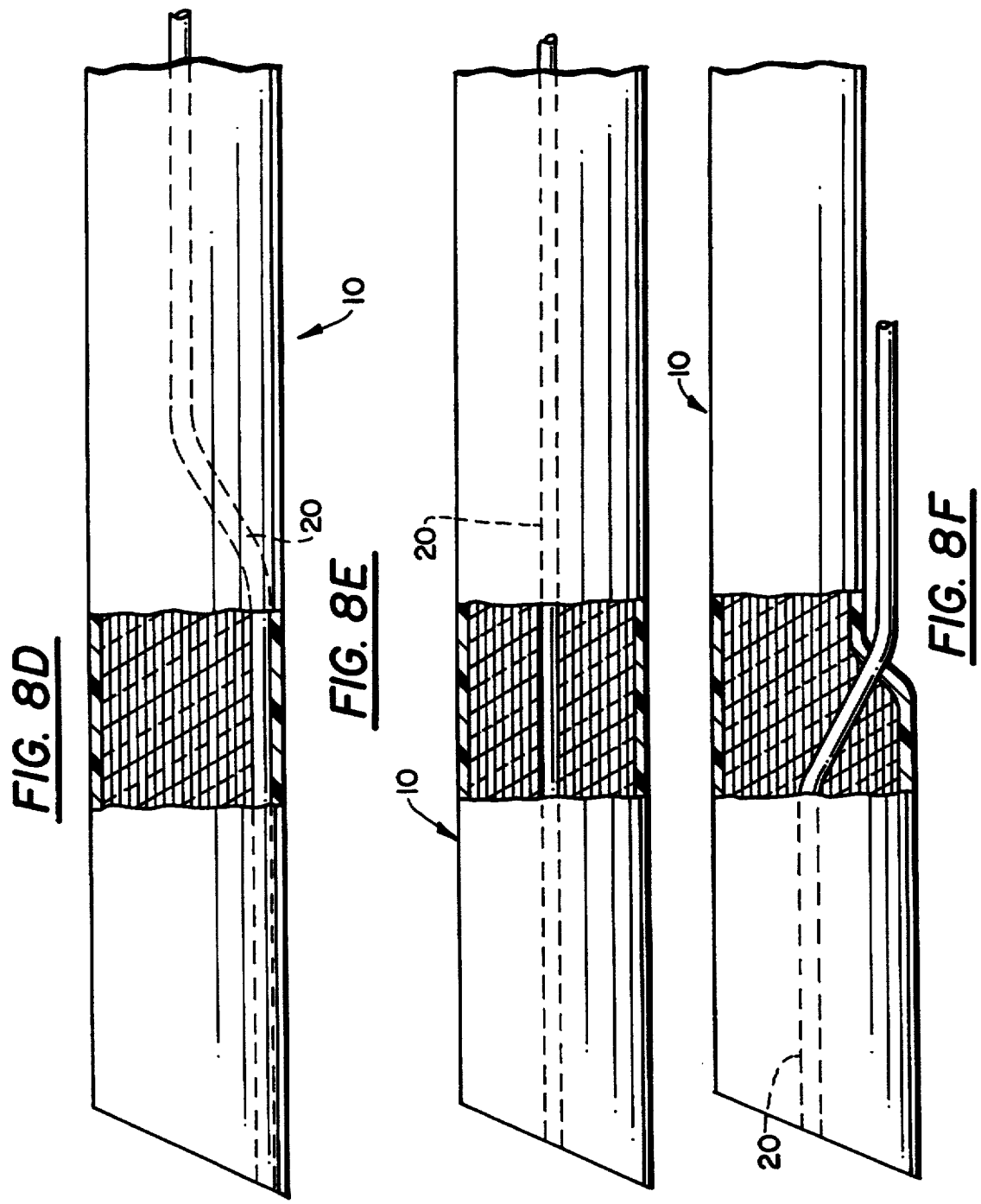

FIBER OPTIC CATHETER WITH TWISTABLE TIP

This is a continuation of application Ser. No. 08/031,391, filed on Mar. 12, 1993, which was abandoned upon the filing hereof, which was a continuation-in-part of application Ser. No. 07/853,607, filed Mar. 18, 1992, now abandoned.

BACKGROUND OF THE INVENTION

1. Field of the Invention

The present invention is directed to a fiber optic catheter, and more particularly to a fiber optic catheter with a twistable tip. The tip can be twisted remotely by rotating the proximal end of a torquing means internal to the catheter. The torquing means may be a torque wire or a guide wire lumen attached to the catheter at or near the distal end.

2. Description Of the Prior Art

Fiber optic catheter assemblies have increasingly been used for probing and clearing obstructions in various vessels such as arteries. The size of the vessel and the distance from the insertion point to the critical region in the vessel determine the characteristics of the catheter to be used. For example, in some situations it is desirable to insert a very thin catheter a considerable distance into a vessel. The catheter must be quite flexible so that it may be steered considerable distances through winding vessel passages.

Once the tip of the catheter reaches the critical point of the vessel passage, it is often desirable to have the tip oriented in a particular direction. It would be ideal if the tip self aligned with the obstruction, however often the tip must be further positioned to carry out an operation. The diameter of the optical fibers in fiber optic catheters is quite small and it is often necessary to continuously move and retarget the optical beam emanating from the optical fibers to ablate a large obstruction. Because the optical fibers are not independently directable inside the catheter, the entire end of the catheter containing the mounted optical fiber must be moved. This problem is addressed by Wells U.S. Pat. No. 4,844,062. The Wells patent discloses an eccentric catheter having optical fibers located off the axial center of the catheter. When the catheter is rotated, the beam from the optical fiber sweeps out a path larger than the diameter of the beam.

A catheter used to traverse considerable distances through a complex anatomy must be flexible. Commonly, the torque to rotate the tip is transmitted through the flexible outer jacket of the catheter. However, the torque applied at the proximal end of the catheter often will not be transferred to the distal end to rotate the tip. Instead the catheter will likely twist and kink under the torsional load. The friction between the catheter and its surroundings over the length of the catheter in a complex anatomy is substantial and the flexible catheter does not have enough torsional rigidity to overcome the friction and transmit torque from its proximal end to its distal end.

One solution to this problem is to increase the stiffness of the catheter wall. This solution has the disadvantage of decreasing the steerability and the ease of insertion of the catheter into a winding passage. This solution is thus limited to short distance and direct insertions.

Flexible catheters do not have sufficient torsional stiffness to be twisted and rigid catheters do not have sufficient flexibility to be inserted into a complex passage. Ideally a catheter should be flexible to permit adequate insertion and steerability while being able to transmit sufficient torque to twist the tip. Additionally the catheter should self align with the obstruction so that a minimum of remote intervention is required. The known art does not disclose any device to self align the tip of a catheter inserted in a complex anatomy. Clark et al. U.S. Pat. No. 5,114,403 discloses a catheter torque mechanism having a torque wire attached to the tip of a catheter and attached to a rotation control mechanism. Clark does not disclose attaching the torque wire to specific points near the catheter tip to achieve specific torque performance, nor does Clark teach altering the material or dimensions of the torque wire to achieve the torque and flexibility profile necessary to be effective in a complex anatomy.

Mueller, Jr., U.S. Pat. No. 4,775,371 discloses a stiffened dilation catheter having a catheter with a section made from material being stiffer or having thicker proximal walls at a distal section of the catheter.

Sampson et al. U.S. Pat. Nos. 4,573,470 and 4,641,654 disclose steerable catheters having a rotatable guide wire. However, the guide wire does not impart any rotation or torque to the tip of the catheter. Gould et al. U.S. Pat. No. 5,055,109 and Gaiser et al. U.S. Pat. No. 4,998,917 disclose steerable catheters with torque transmitting assemblies. However, these inventions disclose deflecting the tip so that it is steerable, not twisting the tip.

A common feature required for most steerable catheters is a turning means at the proximal end of the catheter. Common turning and turn limiting devices are disclosed by Frisbie et al. U.S. Pat. Nos. 4,664,113 and 4,619,263. These patents disclose screw and thread devices which impart an axial dislocation of a wire employed to steer a catheter.

SUMMARY OF THE INVENTION

The present invention addresses the above deficiencies by providing a catheter with a tip which may be remotely twisted by transmitting torque necessary to rotate the tip through a torque transmitting means extending inside the catheter and fixed to the catheter at or near the distal end, thus eliminating the need to rotate the entire catheter to align the tip. The torque transmitting means may be a torque wire or a torquable guide wire lumen. The torque wire or guide wire lumen protrudes from the catheter at the proximal end and can be fixed to a turn limiter for rotating the torque wire or guide wire lumen relative to the catheter and for preventing over-torquing of the torque transmitting means. All catheters disclosed and claimed herein may be operated with any of the turn limiters of the copending continuation-in-part application to Hammersmark et al., filed concurrently herewith, the subject matter of which is hereby incorporated by reference.

The torque transmitting means is attached to the catheter such that when the proximal end of the torque wire or lumen is turned, torque is applied to and twists only the distal end of the catheter. When a torque wire is used, the torque wire may be attached to the catheter by a number of techniques including attaching the wire to the catheter itself or to optical fibers in the catheter near the distal face, attaching the wire to a torque ring near the distal face, attaching the wire to a fixed inner lumen at or near the distal face, and employing a guide wire as a selectively attachable torque wire at the distal tip. Thus a flexible catheter can be inserted into a complex passage and the tip can be twisted without rotating the entire catheter and transmitting torque through its flexible walls.

To aid in accurate positioning of the distal face relative to an obstruction and to aid in inserting the catheter through complex passages, the tip of the present invention may have an angled distal face or a conical distal face. The angled face necessarily has a distal most edge which first contacts an obstruction and automatically turns the face to slide along the obstruction until the entire angled face contacts the obstruction. As a result, the tip self aligns with the obstruction to provide a more efficient orientation for ablating the obstruction.

A conical face has a distal-most portion at the center of a cross section of the catheter. The conical face ensures that the catheter remains centered in the vessel as it is inserted, and it resists becoming caught on obstructions.

BRIEF DESCRIPTION OF THE DRAWINGS

These and other objects and advantages of this invention will become apparent and more readily appreciated from the following detailed description of the presently preferred exemplary embodiments of the invention in conjunction with the accompanying drawings, of which:

FIG. 1 is an elevation, partially broken-out view of a fiber optic catheter with twistable tip according to an embodiment of the present invention;

FIG. 2 is an end view of the distal end of the catheter shown in FIG. 1;

FIG. 3 is an elevation of a fiber optic catheter with twistable tip according to yet another embodiment of the present invention;

FIGS. 8a–8f are schematic views of various fiber optic catheters with a twistable self aligning tip according to the present invention.

DETAILED DESCRIPTION OF THE PRESENTLY PREFERRED EXEMPLARY EMBODIMENTS

Figure 1A:
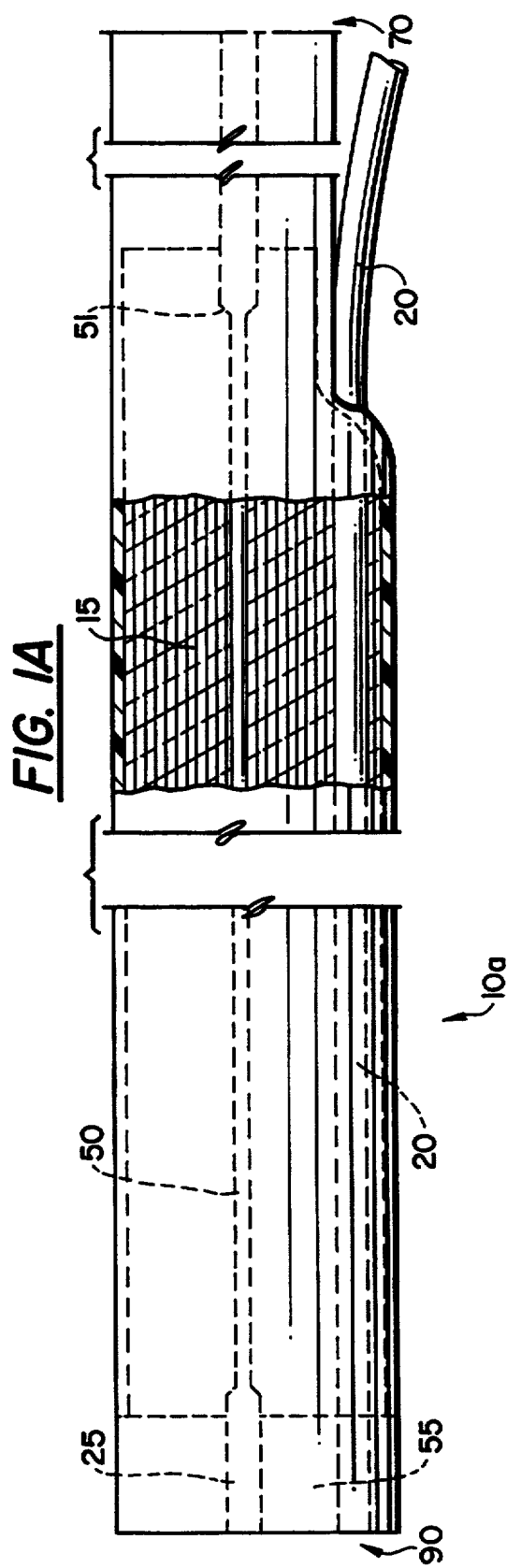
FIG. 1A is an elevation, partially broken-out view of a fiber optic catheter with a twistable tip according to another embodiment of the present invention.

FIG. 1 illustrates a catheter 10 made of conventional materials and containing an inner lumen 20. Inner lumen 20 contains a guide wire used to direct the catheter through the passages of a vessel. Inner lumen 20 is exposed at the distal end 90 of catheter 10. The remaining space inside catheter 10 is filled with optical fibers 15 which are exposed at the distal tip 55.

Catheter 10 is also provided with a means to remotely twist the tip. This is accomplished by a torque wire 50 which extends through the catheter and is attached at the distal tip 55.

A torque wire 50 extends from the proximal end 70 of the catheter 10 through the catheter to its attachment point near the distal end 90. Torque wire 50 is rigidly attached to the distal portion of the catheter such that torque of the torque wire is transmitted to and twists the distal tip. The distal tip 55 of the catheter can be made of a radiopaque material such as metal to aid in viewing the position of the catheter.

As shown in FIGS. 1, 1A and 3, the torque wire 50 may have one or more tapers 51 near the distal end to increase the flexibility and steerability of the catheter and obtain the proper torsional stiffness of torque wire 50. For example, the torque wire 50 may be 0.018 inch in diameter through the body of the catheter and may taper to 0.008 inch and further to 0.005 inch in diameter. The torque wire tip 25 can also be flattened to provide a larger surface for bonding to the distal end of the catheter.

Figure 5A:
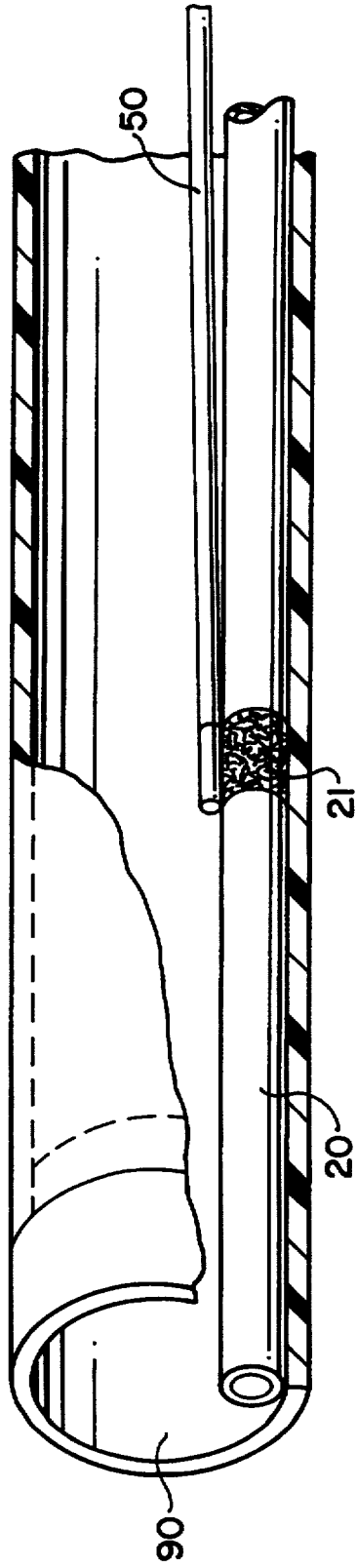
FIG. 5a is a schematic view of a third embodiment of the present invention.
Figure 5B:
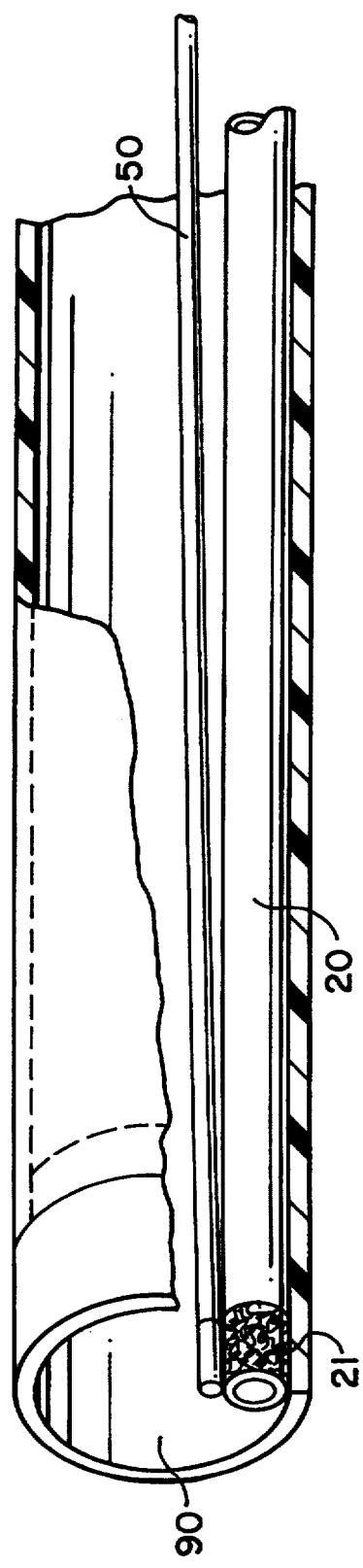
FIG. 5b is a schematic view of a fourth embodiment of the present invention.

The distal end of the torque wire may be attached directly to the catheter wall, or to the inner lumen 20, as shown in FIG. 5a. The point of attachment 21 may be at the distal tip, FIG. 5b, or at a distance back from the distal tip, as shown in FIG. 5a. The location of the point of attachment 21 is determined by the flexibility and torque response characteristics desired. Although the torque wire may be attached to the inner lumen up to 30 cm from the distal face, the ideal attachment position is approximately 3–10 cm from the distal face. A significant advantage of attaching the torque wire to the inner lumen at a position back from the distal tip is that the portion of the catheter beyond the attachment point can be made more flexible for passing through complex passages. Also, this embodiment can provide better torque response at the tip because, depending upon the materials chosen, the inner lumen can transmit the torque to the tip better than a small diameter torque wire.

Figure 4:
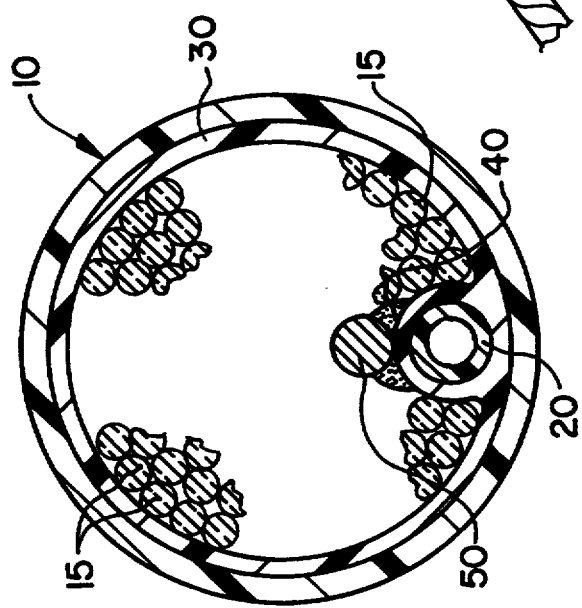
FIG. 4 is a cross-sectional view of Section 4—4 of FIG. 3.

Alternatively, the torque wire is attached to the tip of the catheter by bonding the distal end with the optical fibers 15 in an adhesive matrix, as shown in FIGS. 1 and 2. The torque wire may also be attached to a torque ring which is fixed in the catheter near the distal end. See FIGS. 3 and 4. The torque ring 30 is attached to the catheter so that a torque applied to the torque ring is transmitted to the catheter 10. Torque wire 50 of this embodiment has at least one taper 51 near the distal end, to increase the steerability of the catheter. In fact, torque wire 50 can have the same tapered form as described above. The torque wire is attached to the torque ring by an adhesive bond or weld 40 or other common attaching means. The torque ring may be of any material having sufficient strength and can be made radiopaque to aid in positioning the distal tip 90 of the catheter.

Figure 2A:
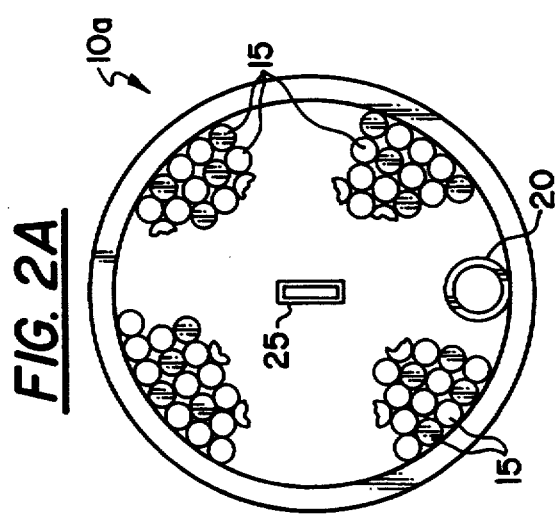
FIG. 2A is an end view of the distal end of the catheter shown in FIG. 1A.

As shown in FIGS. 1A and 2A, in one embodiment of the present invention, torque wire 50 and catheter 10a share a common axis at distal end 90 of catheter 10a.

Figure 7:
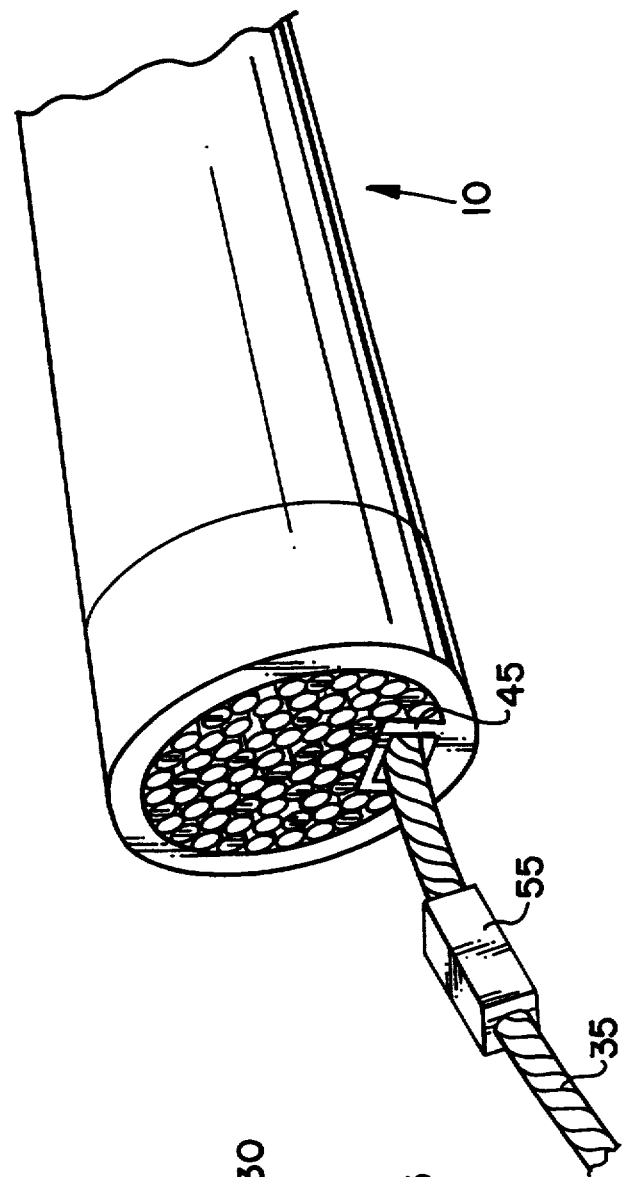
FIG. 7 is a perspective view of a fiber optic catheter with twistable tip according to yet another embodiment of the present invention.

Another technique for rotating the distal end of the catheter is by a key and slot mechanism, shown in FIG. 7. In this embodiment, the guide wire is transformed into a torque wire by sliding a key shaped block 55 into a keyed receiving slot 45 of the inner lumen. The key 55 is rigidly attached to guide/torque wire 35 so that rotating guide/torque wire 35 necessarily rotates key 55. When the tip of the catheter is properly positioned in the vessel, guide/torque wire 35 is retracted into lumen 20. Key 55 is drawn into and rotatably locked to slot 45. If the guide/torque wire 35 is now rotated, torque is applied through the key and slot to twist the distal tip of the catheter. The key shaped block may alternatively be an adhesive, solder, or other material applied to the guide wire and formed into a non-round shape corresponding to any non-round shape of the inner lumen. The guide/torque wire of this embodiment may taper one or more times near the distal end to increase steerability of the catheter. The key and slot alternative of attaching the torque wire to the distal end of the catheter is particularly advantageous because it results in a more flexible catheter. By combining the functions of both the torque wire and guide wire into one wire, interior space is preserved and a reduction of the complexity and cost of the catheter is achieved.

Figure 6:
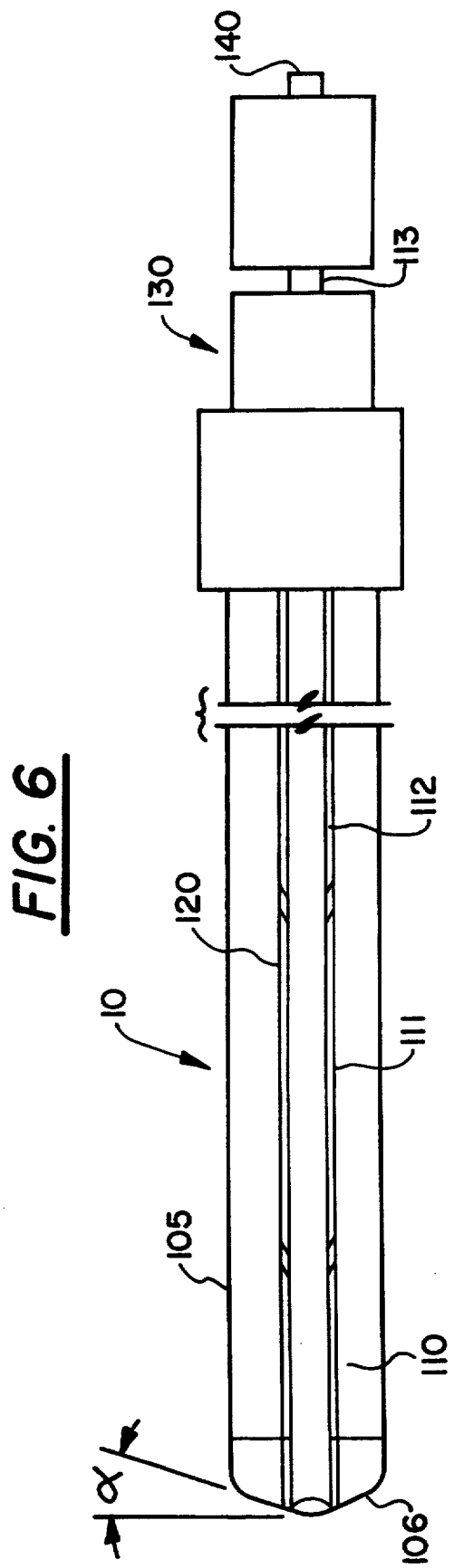
FIG. 6 is a schematic view of a fifth embodiment of the present invention.

Another embodiment of the invention shown in FIG. 6 combines the function of a guide wire lumen and the function of the torque wire. In this embodiment, a guide wire lumen 120 replaces the torque wire of the previous embodiments and provides torque to the distal end. The guide wire lumen 120 is attached to the catheter wall 105 at or near the distal end of the catheter but is otherwise not fixed to the interior of the catheter. The guide wire lumen extends over substantially the length of the catheter and may have a number of discrete sections 110, 111, 112 composed of different materials so as to achieve the desired torque response and flexibility. For example, a torquable inner lumen may have three sections: a distal tip section 110 of standard inner lumen material connected to a section of reinforced lumen 111 followed by a proximal section of hypotube 112 which extends to the proximal end of the catheter.

The distal section 110 may be unreinforced to provide increased flexibility. The standard inner lumen material may be polyethylene, polyester, teflon, polyimide, etc. The reinforced section 111 may comprise a lumen with a coil or braid of reinforcing material encapsulated within the standard inner lumen material. The reinforcing material may be stainless steel or Kevlar. The proximal section 112 may be NiTi or Stainless Steel hypotube to provide efficient torque response through most of the length of the catheter, while allowing a guide wire to pass therethrough. Because of the stiffness of the hypotube, the proximal section does not extend to the distal end of the catheter but connects with the reinforced section about 25 cm from the distal end. The distal-most portion and the reinforced portion together extend the remaining distance to the distal tip of the catheter 10. The lengths and number of sections may be varied to achieve the desired torque response and flexibility profile at the tip. The torquable guide wire lumen, therefore, may have more or fewer material transitions, depending upon the desired torque characteristics of the catheter.

The advantage of the torquable guide wire lumen over the torque wire are numerous. The catheter can be built with one less element, the torque wire, thus freeing up space and improving the flexibility of the catheter. A catheter with a torquable guide wire lumen can provide better torque response than a catheter with a torque wire. Also, using a torquable guide wire lumen allows for a straight exit path for the torque and guide wire element at the proximal end of the catheter system. Normally, the torque wire and the guide wire lumen would have different exit paths at the turn limiter, thus, one of the elements would have a curved exit path. Catheter 10 terminates at a torque knob assembly 130 having a hollow axle 113 extending therethrough. The guide wire lumen communicates with the hollow axle thus providing a guide wire insertion point 140 for the catheter.

When inserting a catheter into a vessel, it is desirable to have the catheter self align to the extent possible with the obstruction. One feature of the present invention provides a self aligning twistable tip. See FIGS. 8a–8f. The catheter 10 comprises an inner lumen 20 and is packed with optical fibers 15. The fibers terminate at the distal face which is angled. The face is made at an angle $\alpha$ relative to a perpendicular to the axis of the catheter which is greater than 0 degrees and preferably about 23°, such that when the catheter 10 is advanced into the vessel over a guide wire passing through lumen 20, the distal most point of the face contacts the obstruction and twists the face and tip to slide over the obstruction until all or most of the angled face contacts the obstruction. This twistable tip with angled face is applicable to catheters having concentric (FIGS. 8e and 8f), or eccentric (FIGS. 8a–8d) guide wires and whether the guide wires extend the length of the catheter (FIGS. 8d and 8e) or are of the short guide lumen variety (FIGS. 8c and 8f). Catheter 10 may be any of the catheters in FIGS. 8a–8f, this means that any of the twistable catheters previously discussed may have an angled face.

Additionally, an angled catheter tip face facilitates insertion of the catheter through a passage. While a catheter with a flat distal face perpendicular to the axis of the catheter may be impeded by obstacles which contact the flat face near the edges, an angled face will deflect off obstructions and continue through the passage.

Referring to FIG. 6, such an angled catheter tip is ideally shaped conically 106. Such a conical face may be concentric with the axis of the catheter as shown, or it may be eccentric such that the tip is offset from the center of the catheter. A conical shape rather than a single angled face provides a deflecting surface in all directions. The conical surface 106 of the present invention makes an angle $\alpha$ of about 23° with a plane perpendicular to the axis of the catheter. Greater angles may cause total internal reflection of optical energy exiting through the fiber faces. An angled tip catheter of this sort may be either eccentric or concentric with respect to an inner lumen. A conical face, centered either on the longitudinal axis of the catheter or the longitudinal axis of the guide wire lumen, or eccentric relative to both the catheter and the lumen may be used with any of the catheters 10, described above.

The torque wire 50, guide/torque wire 35, or torquable inner lumen (referred to hereinafter collectively as a torque element) of the present invention is composed of any suitable material of sufficient lateral flexibility but strong torsional rigidity. The torque element is attached to the catheter at only one attachment point. In all other locations, the torque element rotates freely inside the catheter. It is not necessary that the axis of the torque element and the axis of the catheter be the same at the attachment point. A torque element attached to the catheter off of the catheter axis will provide twisting motion of the tip, not around the axis of the torque wire.

At the proximal end of the catheter, the torque element protrudes from the catheter and is attached to a turn limiter. A turn limiter refers to any of the devices in the copending continuation-in-part application filed concurrently herewith. A turn limiter provides a means to rotate the torque element to provide torque to the distal end, and also a means to limit the torque applied to the torque element to prevent damage to the catheter system. When the torque element is rotated at the proximal end of the catheter 10, torque is transmitted through the catheter to the attachment point where the torque is applied to the catheter thus twisting the tip.

The amount of twist of the catheter tip is determined by the amount of rotation of the torque element applied at the proximal end, the flexibility of the catheter wall and the rigidity of the torque element. Ideally, the distal section of the catheter is more flexible than the remainder of the catheter. The flexibility of the distal section of the catheter can be increased by replacing a distal section of the normal catheter wall with a more flexible catheter material, or by changing the wall thickness of the outer lumen near the distal end, or a combination of differing materials and differing wall thickness. A flexible distal section of the catheter improves the trackability of the catheter upon insertion into a vessel and also improves the twistability of the distal tip. Ideally, a distal section of about 4–30 cm may be provided with a flexibility feature as described above.

If too much torque is applied to the torque wire, damage may occur to a number of components of the catheter. The flexible walls of the distal end of the catheter, the optical fibers, the torque element, and also the surrounding vessel are all susceptible to damage from over-torquing the torque element. Thus, a turn limiting device is connected to the proximal end of the torque element which limits the number of rotations that may be applied to the torque element relative to the catheter.

Although only a few embodiments of this invention have been described in detail above, those skilled in the art will readily appreciate that many modifications and combinations are possible without materially departing from the novel teachings of this invention. Accordingly all such modifications are intended to be included within the scope of this invention.

What is claimed is:

1. A catheter assembly with a twistable tip, comprising:
   a catheter having a distal end;
   a plurality of optical fibers disposed in the catheter and having distal ends extending to the distal end of the catheter; and
   a torque wire extending through the catheter and bonded to the optical fibers near the distal end of the catheter;
   such that when a proximal end of the torque wire is rotated, torque is transferred through the torque wire to the distal end of the catheter thus twisting the tip of the catheter.

2. A catheter assembly with a twistable tip as in claim 1, wherein the torque wire is bonded among the optical fibers in an adhesive matrix at the distal end of the catheter.

3. A catheter assembly with a twistable tip as in claim 1, wherein the torque wire is bonded near the distal end of the catheter such that a longitudinal axis of the torque wire is offset from a longitudinal axis of the catheter at the distal end of the catheter.

4. A catheter assembly with a twistable tip as in claim 1, wherein a distal section of the catheter is more flexible than a remainder of the catheter.

5. A catheter assembly with a twistable tip as in claim 4, wherein the distal section has a length of about 4–30 cm.

6. A catheter assembly as in claim 4, wherein the distal section of the catheter has a thinner wall than the remainder of the catheter.

7. A catheter assembly with a twistable tip as in claim 1, wherein the catheter assembly further comprises a guide wire lumen extending from a distal end of the catheter and terminating distal to the proximal end of the catheter.

8. A catheter assembly with a twistable tip as in claim 1, wherein the torque wire has at least one tapered portion near the distal end of the catheter.

9. A catheter assembly with a twistable tip comprising:
   a catheter having a distal end;
   a plurality of optical fibers disposed in the catheter and having distal ends extending to the distal end of the catheter; and
   a torque wire extending through the catheter such that when a proximal end of the torque wire is rotated, torque is transferred through the torque wire to the distal end of the catheter thus twisting the tip of the catheter, wherein the torque wire is bonded near the distal end of the catheter such that the torque wire and the catheter share a common axis at the distal end of the catheter.

10. A catheter assembly with a twistable tip, comprising:
    a catheter having a distal section that is more flexible than a remainder of the catheter, wherein the distal section of the catheter is composed of a more flexible material than the remainder of the catheter;
    a plurality of optical fibers disposed in the catheter and having distal ends extending to the distal end of the catheter; and
    a torque wire extending through the catheter and bonded to at least one of the optical fibers and the catheter near the distal end such that when a proximal end of the torque wire is rotated, torque is transferred through the torque wire to the distal end of the catheter thus twisting the tip of the catheter.

11. A catheter assembly as in claim 10, wherein the distal section of the catheter also has a thinner wall than the remainder of the catheter.

12. A catheter assembly with a twistable tip, comprising:
    a catheter having a distal end, wherein a plane of a distal face of the catheter is not perpendicular to a longitudinal axis of the catheter;
    a plurality of optical fibers disposed in the catheter and having distal ends extending to the distal end of the catheter; and
    a torque wire extending through the catheter and bonded to at least one of the optical fibers and the catheter near the distal end such that when a proximal end of the torque wire is rotated, torque is transferred through the torque wire to the distal end of the catheter thus twisting the tip of the catheter.

13. A catheter assembly with a twistable tip as in claim 12, wherein the distal face is at an angle of about 23 degrees to a plane perpendicular to the longitudinal axis of the catheter.

14. A catheter assembly with a twistable tip as in claim 12, wherein the catheter includes an eccentric guide wire lumen and the distal face is angled such that the eccentric guide wire lumen is exposed at a distal-most portion of the distal face.

15. A catheter assembly as in claim 14, wherein the eccentric guide wire lumen extends from a distal end of the catheter and terminates at a location distal to a proximal end of the catheter.

16. A catheter assembly as in claim 12, wherein the catheter includes a guide wire lumen concentric with the catheter at the distal face.

17. A catheter assembly as in claim 16, wherein said plane is at an angle of about 23 degrees with respect to a plane perpendicular to the longitudinal axis of the catheter.

18. A catheter assembly with a twistable tip comprising:
- a catheter having a distal end, wherein the catheter includes a guide wire lumen concentric with the catheter at the distal face;
- a plurality of optical fibers disposed in the catheter and having distal ends extending to the distal end of the catheter; and
- a torque wire extending through the catheter and bonded to at least one of the catheter and the optical fibers near the distal end such that when a proximal end of the torque wire is rotated, torque is transferred through the torque wire to the distal end of the catheter thus twisting the tip of the catheter.

19. A catheter assembly with a twistable tip comprising:
- a catheter having a distal end;
- a plurality of optical fibers disposed in the catheter and having distal ends extending to the distal end of the catheter; and
- a torque wire extending through the catheter and bonded to at least one of the catheter and the optical fibers near the distal end such that when a proximal end of the torque wire is rotated, torque is transferred through the torque wire to the distal end of the catheter thus twisting the tip of the catheter, wherein the torque wire has at least one tapered portion near the distal end of the catheter such that the torque wire tapers from a diameter of about 0.018 to about 0.008 inches and may taper further to about 0.005 inches in diameter.

20. A catheter assembly with a twistable tip comprising:
- a catheter having a distal end;
- an inner lumen extending from the distal end to a proximal end within the catheter;
- optical fibers extending through the catheter from the distal to the proximal end;
- a torque wire extending through the catheter and bonded to at least one of the inner lumen and the optical fibers at the distal end of the catheter, wherein the torque wire is bonded among the optical fibers in an adhesive matrix when the torque wire is bonded to the optical fibers, such that when a proximal end of the torque wire is rotated, torque is transferred through the torque wire to the distal end of the catheter.

21. A catheter assembly with a twistable tip as in claim 20, wherein a distal section of the catheter is more flexible than a remainder of the catheter.

22. A catheter assembly with a twistable tip as in claim 21, wherein the distal section of the catheter is composed of a more flexible material than the remainder of the catheter.

23. A catheter assembly as in claim 22, wherein the distal section of the catheter has a thinner wall than the remainder of the catheter.

24. A catheter assembly with a twistable tip as in claim 21, wherein the distal section has length of about 4-30 cm.

25. A catheter assembly with a twistable tip as in claim 20, wherein a distal face of the catheter is not perpendicular to a longitudinal axis of the catheter.

26. A catheter assembly with a twistable tip as in claim 25, wherein the distal face is at an angle of about 23 degrees to a plane perpendicular to a longitudinal axis of the catheter.

27. A catheter assembly with a twistable tip as in claim 25, wherein the catheter includes an eccentric guide wire lumen and the distal face is angled such that the eccentric guide wire lumen is exposed at a distal-most portion of the distal face.

28. A catheter assembly with a twistable tip as in claim 20, wherein a distal face of the catheter is a cone.

29. A catheter assembly with a twistable tip as in claim 28, wherein the distal face is at an angle of about 23° to a plane perpendicular to a longitudinal axis of the catheter, such that a distal most point of the catheter is at a center of the catheter in cross-section.

30. A catheter assembly with a twistable tip as in claim 28, wherein a distal most point of the distal face is not along a longitudinal axis of the catheter.

31. A catheter assembly with a twistable tip as in claim 20, wherein the catheter assembly further comprises a guide wire lumen extending from a distal end of the catheter and terminating distal to the proximal end of the catheter.

32. A catheter assembly with a twistable tip as in claim 20, wherein the catheter includes a guide wire lumen concentric with the catheter at the distal face.

33. A catheter assembly with a twistable tip as in claim 20, wherein the torque wire has at least one tapered portion near the distal end of the catheter.

34. A catheter assembly with a twistable tip as in claim 20, wherein the torque wire tapers from a diameter of about 0.018 to about 0.008 inches and tapers further to about 0.005 inches in diameter.

35. A catheter assembly with twistable tip comprising:
- a catheter having a distal end;
- an inner lumen extending from the distal end to a proximal end within the catheter;
- a torque wire extending through the catheter and bonded to the inner lumen at a point back from the distal end;
- such that when a proximal end of the torque wire is rotated, torque is transferred through the torque wire to the inner lumen and subsequently to the distal end of the catheter.

36. A catheter assembly with twistable tip as in claim 35, wherein the torque wire is attached to the inner lumen at a distance of up to 30 cm from the distal end.

37. A catheter assembly with twistable tip as in claim 36, wherein a distal section of the catheter is more flexible than a remainder of the catheter.

38. A catheter assembly with twistable tip as in claim 37, wherein the distal section of the catheter is composed of a more flexible material than the remainder of the catheter.

39. A catheter assembly with twistable tip as in claim 37, wherein the distal section has length of about 4-30 cm.

40. A catheter assembly with twistable tip as in claim 37, wherein the distal section of the catheter has a thinner wall than the remainder of the catheter.

41. A catheter assembly with twistable tip as in claim 35, wherein the torque wire is attached to the inner lumen at a distance of 6 to 10 cm from the distal end.

42. A catheter assembly with a twistable tip as in claim 41, wherein a distal face of the catheter is a cone.

43. A catheter assembly with a twistable tip as in claim 42, wherein the distal face of the catheter is at an angle of about 23° to a plane perpendicular to a longitudinal axis of the catheter, such that a distal-most point of the catheter is at a center of the catheter in cross section.

44. A catheter assembly with twistable tip as in claim 42, wherein a distal most point of the distal face is not along a longitudinal axis of the catheter.

45. A catheter assembly with twistable tip as in claim 41, wherein the catheter assembly further comprises a guide wire lumen extending from a distal end of the catheter and terminating distal to the proximal end of the catheter.

46. A catheter assembly with twistable tip as in claim 35, wherein a distal face of the catheter is not perpendicular to a longitudinal axis of the catheter.

47. A catheter assembly with twistable tip as in claim 46, wherein the distal face is at an angle of about 23 degrees to a plane perpendicular to a longitudinal axis of the catheter.

48. A catheter assembly with twistable tip as in claim 46, wherein the catheter includes an eccentric guide wire lumen and the distal face is angled such that the eccentric guide wire lumen is exposed at a distal-most portion of the distal face.

49. A catheter assembly with twistable tip as in claim 35, wherein the catheter includes a guide wire lumen concentric with the catheter at the distal face.

50. A catheter assembly with twistable tip as in claim 35, wherein the torque wire has at least one tapered portion near the distal end of the catheter.

51. A catheter assembly with twistable tip as in claim 35, wherein the torque wire tapers from a diameter of about 0.018 to about 0.008 inches and tapers further to about 0.005 inches in diameter.

* * * * *